US012571550B2

(12) United States Patent
Sarkar et al.

(10) Patent No.: US 12,571,550 B2
(45) Date of Patent: Mar. 10, 2026

(54) ULTRAVIOLET LIGHT FILTER ASSEMBLY

(71) Applicants: Pritam Kumar Sarkar, Toronto (CA);
Subhendu Chandra, Kolkata (IN)

(72) Inventors: Pritam Kumar Sarkar, Toronto (CA);
Subhendu Chandra, Kolkata (IN)

( * ) Notice: Subject to any disclaimer, the term of this
patent is extended or adjusted under 35
U.S.C. 154(b) by 1074 days.

(21) Appl. No.: 17/382,051

(22) Filed: Jul. 21, 2021

(65) Prior Publication Data

US 2022/0136719 A1     May 5, 2022

Related U.S. Application Data

(60) Provisional application No. 63/058,557, filed on Jul.
30, 2020.

(51) Int. Cl.
*F24F 8/22*     (2021.01)
*A61L 9/20*     (2006.01)
*B01D 46/00*    (2022.01)
*F24F 3/16*     (2021.01)

(52) U.S. Cl.
CPC    *F24F 8/22* (2021.01); *A61L 9/20* (2013.01);
*B01D 46/0028* (2013.01); *F24F 3/16*
(2013.01)

(58) Field of Classification Search
CPC ....... F24F 8/22; F24F 3/16; A61L 9/20; A61L
2209/14; A61L 2209/16; B01D 46/0028;
B01D 46/10
See application file for complete search history.

(56) References Cited

U.S. PATENT DOCUMENTS

| | | |
|---|---|---|
| 5,790,934 A | 8/1998 | Say et al. |
| 6,136,058 A | 10/2000 | Miller |
| 6,764,533 B2 | 7/2004 | Lobiondo, Jr. |
| 6,884,399 B2 | 4/2005 | Reisfeld et al. |
| 7,704,463 B2 | 4/2010 | Willette |
| 9,339,579 B2 | 5/2016 | Willette |
| 9,726,388 B2 | 8/2017 | Goel |
| 10,161,641 B2 | 12/2018 | Goel |
| 2006/0254298 A1 | 11/2006 | Witham |
| 2006/0278075 A1* | 12/2006 | Blackner ................ B03C 3/016 95/57 |
| 2007/0059225 A1 | 3/2007 | Willette |
| 2010/0219259 A1 | 9/2010 | Starcic |
| 2011/0011112 A1 | 1/2011 | Goel |
| 2017/0321910 A1 | 11/2017 | Goel |
| 2020/0360858 A1 | 11/2020 | Mathur |

(Continued)

FOREIGN PATENT DOCUMENTS

| | | | |
|---|---|---|---|
| CN | 105251356 A | * | 1/2016 |
| IN | 201841034954 A | | 9/2019 |
| IN | 202121000499 A | | 1/2021 |

OTHER PUBLICATIONS

CN 105251356 A (English Translation) (Year: 2016).*

*Primary Examiner* — Maris R Kessel
*Assistant Examiner* — Nebyate Seged

(57)     ABSTRACT

An ultraviolet light filter assembly includes a filter and an
ultraviolet light assembly. The filter is coupled to the ultra-
violet light assembly. When the air flows through the ultra-
violet light filter assembly, the filter absorbs particles that are
present in the air. However, ultraviolet light assembly pro-
vides UVC light that damage RNA and DNA of the patho-
gens present in the air. As a result, the air becomes more
purified after passing through the ultraviolet light filter
assembly.

7 Claims, 3 Drawing Sheets

(56)  References Cited

U.S. PATENT DOCUMENTS

| 2022/0196266 A1* | 6/2022 | Solseth | F24F 8/10 |
| 2023/0039310 A1* | 2/2023 | Baarman | A61L 9/20 |
| 2023/0272928 A1* | 8/2023 | Livchak | F24F 13/06 |
| | | | 422/121 |

* cited by examiner

ULTRAVIOLET LIGHT FILTER ASSEMBLY

FIELD

This application is related to the field of air filtration specifically in heating, ventilation and air conditioning unit also known as HVAC.

BACKGROUND OF THE INVENTION

Usually, heating, ventilation and air conditioning (HVAC) systems consist of a centralized heating and/or air conditioning unit connected to a blower that circulates heated or cooled air throughout a building via ducts. Centralized systems are seen in a number of settings such as buildings, cruise ships, trains, and vehicles. There are some advantages of such a system. For example, centralized HVAC systems are quieter, less drafty, easier to maintain and often have space for higher efficiency air filters. In operation, much of the air within a building is recirculated while mixing the recirculated air with fresh air from an external source. Such recirculation reduces overall energy costs because the recirculated air does not need to be heated or cooled continuously but need only to be maintained at a proper interior temperature.

The recirculation of air, however, has certain drawbacks. Although HVAC systems have air filters to remove particulate matters from the airstream, the ventilation ducts of the HVAC system can become contaminated with bacteria, viruses and/or molds, thereby contaminating the airflow which is directly sent into rooms where people are breathing. Contaminated HVAC ducts have been associated with so called Sick Building Syndrome (SBS) as well as with Norwalk virus contamination on cruise ships. It is, therefore, necessary to take steps to prevent contamination, or once contamination has taken place, to disinfect the duct.

The air filtration in centralized system is a primary requirement to safeguard the blower from being damaged by suspended particles that may be sucked in through the inlet. In the process, the air filtration increases the air quality and the life of the blower and the actuator as well. However, this commonly used filter neither blocks germs and/or viruses nor kills them. Therefore, there is a need to disinfect the circulated air by other means. Ultraviolet light with a wavelength between 180 to 300 nm kills germs, molds and/or viruses, hence, has been widely used for the disinfection of air, water, and surfaces for many years. Wavelength near 253.7 nm, also known as germicidal UVC light, is particularly useful for killing bacteria, virus, fungus, mold and spores and is conveniently generated by low pressure mercury vapor lamp.

SUMMARY

Ultraviolet light filter assembly has been developed for filtering the germs and/or viruses as well as particles from air and/or gas that flows through a duct. Such filters have the similar overall dimensions as a conventional panel-type filter has. The conventional panel-type filter may filter particles but cannot filter and/or kill viruses. In contrast, the ultraviolet light filter has both capabilities—it can kill viruses as well as filter particles. This is because the conventional panel-type filter does not have an ultraviolet light while the ultraviolet light filter has both an ultraviolet light and a conventional filter.

The ultraviolet light filter can be placed into the duct of a centralized heating, ventilation and air conditioning (HVAC)

system and oriented transverse to the direction of the air/gas flow. Usually, the duct has a narrow opening for a filter to be placed. All types of conventional filters are designed to fit into this opening without much leakage to occur. However, the opening is narrow so it faces a challenge to insert an ultraviolet light together with a conventional panel-type filter. Also, the ultraviolet light may block air flow, thereby adding resistance to air flow while degrading the performance of the HVAC system.

DRAWINGS

DESCRIPTION OF VARIOUS EMBODIMENTS

Numerous embodiments are described in this application and are presented for illustrative purposes only. The described embodiments are not intended to be limiting in any sense. The invention is widely applicable to numerous embodiments, as is readily apparent from the disclosure herein. Those skilled in the art will recognize that the present invention may be practiced with modification and alteration without departing from the teachings disclosed herein. Although particular features of the present invention may be described with reference to one or more particular embodiments or figures, it should be understood that such features are not limited to usage in the one or more particular embodiments or figures with reference to which they are described.

The terms "an embodiment," "embodiment," "embodiments," "the embodiment," "the embodiments," "one or more embodiments," "some embodiments" and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

As used herein and in the claims, two or more parts are said to be "coupled," "connected," "attached" or "fastened" where the parts are joined or operate together either directly or indirectly (i.e., through one or more intermediate parts), so long as a link occurs. As used herein and in the claims, two or more parts are said to be "directly coupled", "directly connected", "directly attached", or "directly fastened" where the parts are connected in physical contact with each other. As used herein, two or more parts are said to be "rigidly coupled," "rigidly connected," "rigidly attached" or "rigidly fastened" where the parts are coupled so as to move as one while maintaining a constant orientation relative to each other. None of the terms "coupled," "connected," "attached" and "fastened" distinguish the manner in which two or more parts are joined together.

Figure 1:
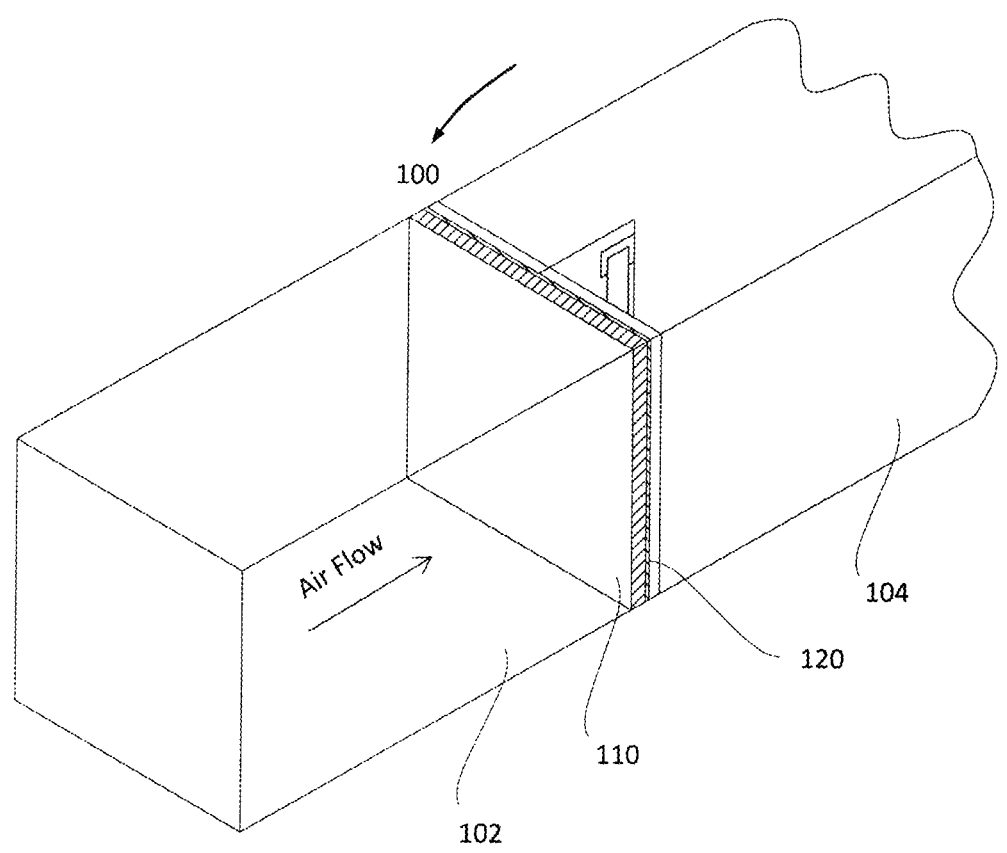
FIG. 1 is a perspective view of an ultraviolet light filter assembly mounted between two air ducts, in accordance with an embodiment.

FIG. 1 shows an ultraviolet light filter assembly 100, which is used to purify air in HVAC system. For example, ultraviolet light filter assembly 100 may be used to clean and disinfect the circulating air in the ducts at its inlet and/or outlet. As shown, a slot is kept in the duct of a HVAC system where a filter needs to be placed. Without the filter, the duct becomes discontinuous and the HVAC system is ineffective for use. The purpose of the filter is to clean the circulating air. However, such a filter is not available that has features like blocking the suspended particles in air as well as killing germs and/or viruses. Ultraviolet light filter assembly 100 does solve this problem. As shown in FIG. 1, air flows through from the left side of the duct 102 to the right side of the duct 104. Placing an ultraviolet light filter assembly 100 in the slot makes the left side of the duct 102 and the right side of the duct 104 continuous. However, the air flow may be obstructed by ultraviolet light filter assembly 100 if the ultraviolet light in ultraviolet light filter assembly 100 is placed improperly. Therefore, the challenge is, the ultraviolet light in ultraviolet light filter assembly 100 is to be placed properly so that the ultraviolet light filter assembly 100 can be inserted into the narrow slot without degrading the performance of the HVAC system.

Still referring to FIG. 1, ultraviolet light filter assembly 100 may include one or more filters 110 that may block suspended particles carried away by the air. As shown, when air flows from duct 102 to duct 104, the air at first, passes through filter 110 where the dust particles in the air are blocked by filter 110. The size of the blocked particles depends on the type of material used in filter media of filter 110. The air may contain pathogens too which are difficult to be blocked. The pathogens are smaller in size and may vary from 0.01 µm to 0.5 µm. Therefore, most of the pathogens pass through the filter without being blocked. Ultraviolet light filter assembly 100 is capable of killing these pathogens that otherwise, could not be blocked, thereby disinfecting the recirculated air.

Figure 2:
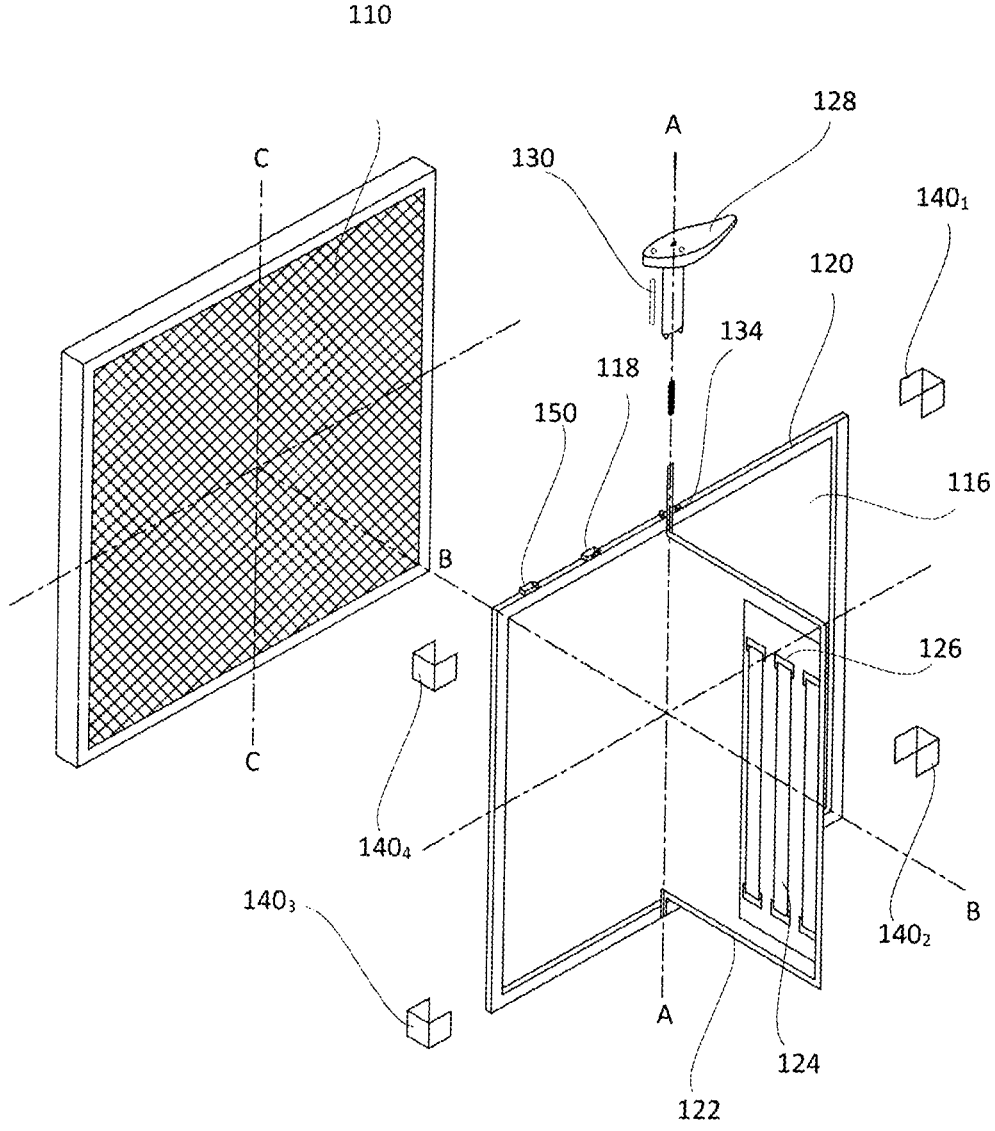
FIG. 2 is an exploded view of the ultraviolet light filter assembly of FIG. 1.

Now referring to FIG. 2, ultraviolet light filter assembly 100 may include an ultraviolet light assembly 116 and a filter 110. In FIG. 2, filter 110 is a panel type filter, however, the shape of filter 110 may have other types depending on the shape of the duct 102 and 104. Filter 110 includes filter media 112 which can absorb particulate matters thereby eliminating dust from the circulating air. Filter media 112 may be made of synthetic plastic, fiber glass, fabric, paper, or similar materials.

Figure 3:
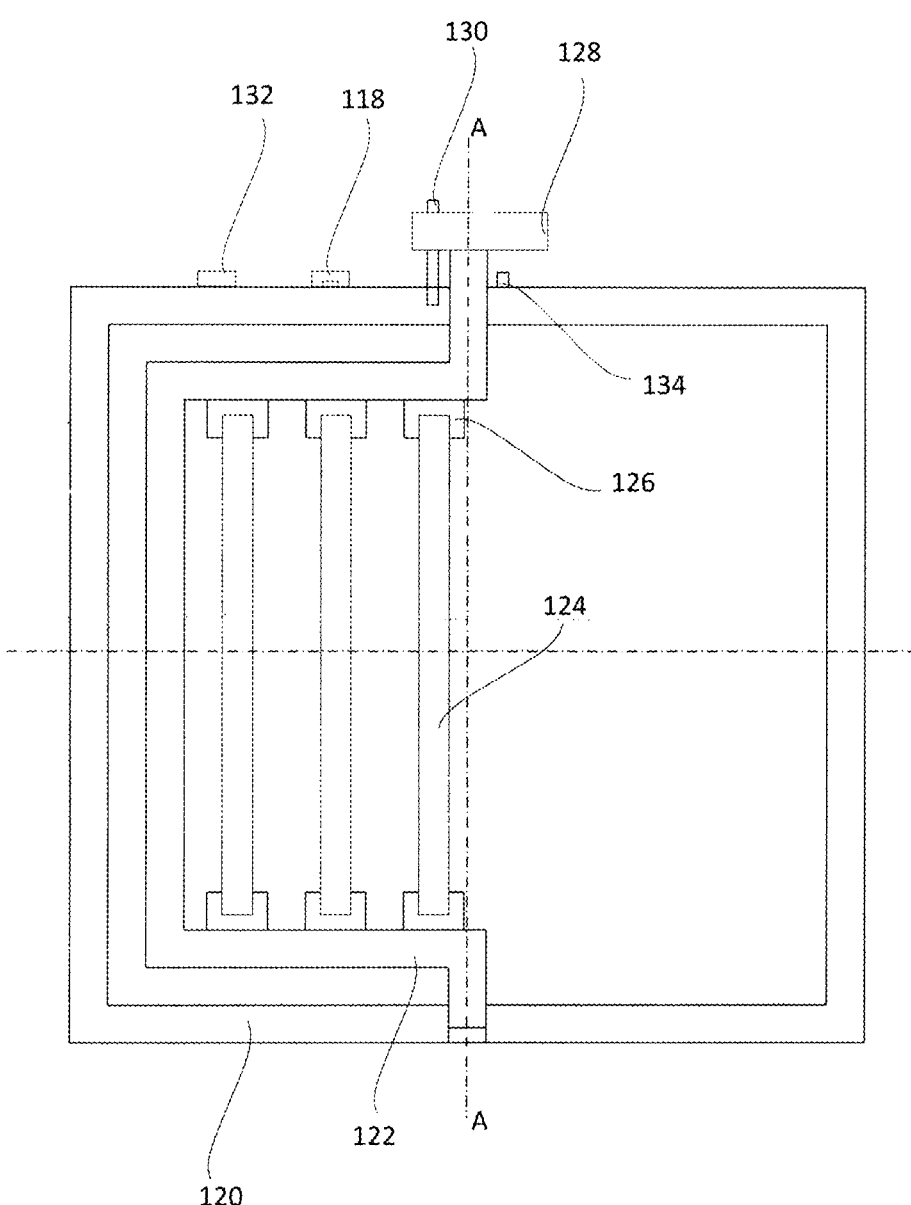
FIG. 3 is a side view of the ultraviolet light assembly.

Referring to FIG. 2 and FIG. 3, ultraviolet light assembly 116 may include a fixed frame 120, a rotatable frame 122 and a handle 128. Rotatable frame 122 is connected to one (or more) ultraviolet light 124 by one (or more) lamp/tube light holder 126. Rotatable frame 122 can be rotated along with ultraviolet light 124 about a vertical axis AA by handle 128. Rotatable frame 122 has two locked positions named folded and unfolded. When it is under folded condition, rotatable frame 122 is aligned with fixed frame 120 and therefore, both rotatable frame 122 and fixed frame 120 are on the same plane. FIG. 3 shows this configuration. Folded condition facilitates the ultraviolet light filter assembly 116 to get into the slot when being inserted. On the other hand, when it is under unfolded condition, rotatable frame 122 is aligned perpendicularly with the plane of fixed frame 120. FIG. 2 shows this configuration. Unfolded condition facilitates the flow of air through the duct without getting obstructed by ultraviolet light 124. This does not disturb the performance of the HVAC system.

Referring to FIG. 2, the flow of air may be along the direction of BB either from left to right or from right to left. When the air flows from left to right, the air, at first, passes through filter 110. Here, the particulate matters are obstructed and absorbed/arrested. However, the pathogens may get some obstruction but cannot be absorbed/arrested as the size of the pathogens are too small compared to the size of the hole in filter 110. Then, the escaped pathogens pass through ultraviolet light assembly 116 and in the process, come to the vicinity of the UVC light which is produced by ultraviolet light 124. It is proven that UVC light is very effective to damage RNA and DNA of the pathogens. The UVC light is also known as ultraviolet germicidal irradiation light. The pathogens in the air are killed by the UVC light. Since the air is recirculated any survived pathogens in the first path is killed during the successive paths of the recirculation process.

Still referring to FIG. 2, when the air flows from right to left along the direction BB, the air, at first, passes through ultraviolet light assembly 116 and the pathogens are killed by the UVC light. In this case, the air gets to pass through filter 110 after passing ultraviolet light assembly 116. However, filter 110 needs to be rotated by 180° about the vertical axis CC for the purpose of effectiveness of filter 110 as the orientation of placing filter 110 depends on the direction of air flow. In contrast, no such adjustment is required in case of ultraviolet light assembly 116 as the effectiveness of ultraviolet light assembly 116 does not depend on the direction of air flow.

Still referring to FIG. 2 and FIG. 3, handle 128 is connected to rotatable frame 122. Therefore, when handle 128 rotates, rotatable frame 122 also rotates along the same direction. Before insertion of ultraviolet light filter assembly 100 into the slot in between the ducts, the plane of rotatable frame 122 is kept parallel to the plane of fixed frame 120. This is also known as folded locked configuration as there is a way to lock this folded configuration. In this configuration, the thickness of ultraviolet light filter assembly 100 must be less than the thickness of the slot so that ultraviolet light filter assembly 100 can enter inside the slot. Again, the thickness of ultraviolet light filter assembly 100 is equal to the sum of the thickness of filter 110 and the thickness of fixed frame 120. The folded locked configuration helps achieve this low thickness. After insertion, rotatable frame 122 may be rotated by rotating handle 128 and is made perpendicular to the plane of fixed frame 120. The angle between the plane of rotatable frame 122 and the plane of fixed frame 120 may vary from 0 to 180°; however, the effectiveness of damaging the ribonucleic acid (RNA) and deoxyribonucleic acid (DNA) of the pathogens varies considerably depending on this angle. The resistance of the air flow depends on this angle too. The most effective angle is 90° and this configuration is known as unfolded locked configuration as again there is a way to lock the rotation of this unfolded configuration. Rotatable frame 122 needs to be locked because it may automatically rotate by the air flow or other means.

Still referring to FIG. 2 and FIG. 3, handle 128 may include a pin 130 that locks the rotation of rotatable frame 122. Pin 130 can connect handle 128 with fixed frame 120. There are two holes on handle 128. These two holes are 90° apart corresponding to the two positions of rotatable frame 122, folded and unfolded. Using pin 130, these two positions of rotatable frame 122 can be locked. Clips 140 is used to connect filter 110 with ultraviolet light assembly 116. There are four clips each for each corner. This combines all the components into one unit.

Referring back to FIG. 2, ultraviolet light assembly 116 may include an electrical connector 118 which connects the external power source with the ultraviolet light 124. The connection between connector 118 and ultraviolet light 124 is controlled by a micro-switch 134 which is normally open. Therefore, ultraviolet light 124 cannot be turned on unless the micro-switch 134 is closed. Since ultraviolet light is dangerous for human health, micro-switch 134 forbids accidental power on of ultraviolet light 124 thereby avoid health hazards to human life.

Still referring to FIG. 2, ultraviolet light filter assembly 100 may include a passive infrared (PIR) sensor 132 that detects motion of living creature such as human and/or animal. Therefore, PIR sensor 132 can detect the presence of a human or pet and acts upon its detection. For example, when there is no human and/or pet moving around PIR sensor 132, PIR sensor 132 detects none so is off. Therefore, there would be no action. However, when there is human and/or pet, PIR sensor 132 detects one so turns on. In this case, if ultraviolet light 124 is on, the circuit automatically shuts off immediately. But if ultraviolet light 124 is off there would be no action. Also, in this case, ultraviolet light 124 cannot be turned on even if micro-switch 134 is closed.

A microcontroller may be communicatively connected to the PIR sensor 132 which may detect a presence or absence of one/more animals. When the PIR sensor 132 detects the presence of the animal, the PIR sensor 132 sends a signal of the presence of the animal to the microcontroller which then shuts off the electrical power immediately thereby shutting off the ultraviolet light 124.

The invention claimed is:

1. An ultraviolet light filter assembly comprising:
at least one filter media;
a panel for holding the filter media;
at least one rotatable frame;
at least one ultraviolet light, removably connectable to the rotatable frame;

a fixed frame encasing and holding the rotatable frame; and
a plurality of outer connectors connecting the fixed frame and the panel when the said ultraviolet light filter assembly is in the assembled condition.

2. The ultraviolet light filter assembly of claim 1, wherein the rotatable frame comprises:
a power supply that supplies power to the ultraviolet light;
a handle that rotates the rotatable frame; and
a pin.

3. The ultraviolet light filter assembly of claim 2, further comprising:
a holder securely connected to the rotatable frame; and
a connector coupled to the ultraviolet light and removably connectable to the holder.

4. The ultraviolet light filter assembly of claim 2, wherein the pin acts as a key to lock the movement of the rotatable frame at one or more positions.

5. An ultraviolet light filter assembly of claim 1, further comprising:
a passive infrared (PIR) sensor; and
a microcontroller that is communicatively connected to the passive infrared sensor.

6. The ultraviolet light filter assembly of claim 5, wherein the passive infrared (PIR) sensor may detect the presence of one or more animals.

7. The ultraviolet light filter assembly of claim 5, wherein the microcontroller may shut off the electrical power when the said microcontroller receives information of a presence of any animal from the passive infrared (PIR) sensor.

* * * * *